US00PP21277P2

(12) United States Plant Patent
Barends

(10) Patent No.: US PP21,277 P2
(45) Date of Patent: Sep. 7, 2010

(54) ***GERANIUM* PLANT NAMED 'FIPELSUMTRUR'**

(50) Latin Name: *Pelargonium×hortorum*
Varietal Denomination: Fipelsumtrur

(75) Inventor: Eveline Barends, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 12/383,280

(22) Filed: Mar. 23, 2009

(51) Int. Cl.
*A01H 5/00* (2006.01)

(52) U.S. Cl. ..... Plt./330
(58) Field of Classification Search ..... Plt./330
See application file for complete search history.

*Primary Examiner*—Susan B McCormick Ewoldt
(74) *Attorney, Agent, or Firm*—C. A. Whealy

(57) ABSTRACT

A new and distinct cultivar of Zonal *Geranium* plant named 'Fipelsumtrur', characterized by its upright and somewhat outwardly spreading growth habit; rounded plant habit; freely basal branching habit; medium green-colored leaves with distinct zonation pattern; early and freely flowering habit; semi-double red-colored flowers; and good garden performance.

1 Drawing Sheet

Botanical designation: *Pelargonium×hortorum*.
Cultivar denomination: 'Fipelsumtrur'.

BACKGROUND OF THE INVENTION

The present invention relates to a new and distinct cultivar of Zonal *Geranium* plant, botanically known as *Pelargonium×hortorum*, and hereinafter referred to by the name 'Fipelsumtrur'.

The new Zonal *Geranium* plant is a product of a planned breeding program conducted by the Inventor in De Lier, The Netherlands. The objective of the breeding program is to create new compact, freely-branching and freely-flowering Zonal *Geranium* cultivars that flower early and have attractive foliage and flower coloration.

The new Zonal *Geranium* plant originated from a cross-pollination made by the Inventor in De Lier, The Netherlands of two unnamed proprietary selections of *Pelargonium×hortorum*, not patented, in August, 2005. The new Zonal *Geranium* was discovered and selected by the Inventor as a single flowering plant from within the progeny of the stated cross-pollination in a controlled greenhouse environment in De Lier, The Netherlands, in March, 2006.

Asexual reproduction of the new Zonal *Geranium* plant by vegetative terminal cuttings in a controlled greenhouse environment in De Lier, The Netherlands, since July, 2006, has shown that the unique features of this new Zonal *Geranium* plant are stable and reproduced true to type in successive generations.

SUMMARY OF THE INVENTION

Plants of the new Zonal *Geranium* have not been observed under all possible environmental conditions. The phenotype may vary somewhat with variations in environment conditions and cultural practices such as temperature, daylength and light intensity without, however, any variance in genotype.

The following traits have been repeatedly observed and are determined to be the unique characteristics of 'Fipelsumtrur'.

These characteristics in combination distinguish 'Fipelsumtrur'as a new and distinct cultivar of Zonal *Geranium:*

1. Upright and somewhat outwardly spreading growth habit; rounded plant habit.
2. Freely basal branching habit.
3. Medium green-colored leaves with distinct zonation pattern.
4. Early and freely flowering habit.
5. Semi-double red-colored flowers.
6. Good garden performance.

Plants of the new Zonal *Geranium* differ primarily from plants of the parent selections in plant size and uniformity as plants of the new *Geranium* are more compact and more uniform than plants of the parent selections.

Plants of the new Zonal *Geranium* can be compared to plants of *Pelargonium×hortorum* 'Fisum Red', disclosed in U.S. Plant patent application Ser. No. 16,106. In side-by-side comparisons conducted in De Lier, The Netherlands, plants of the new Zonal *Geranium* differed from plants of 'Fisum Red' primarily in flower color as plants of 'Fisum Red' had more scarlet red-colored flowers. In addition, leaves of plants of the new Zonal *Geranium* had a more distinct zonation pattern than leaves of plants of 'Fisum Red'.

Plants of the new Zonal *Geranium* can also be compared to plants of *Pelargonium×hortorum* 'Toscana Friesia', not patented. In side-by-side comparisons conducted in De Lier, The Netherlands, plants of the new Zonal *Geranium* differed from plants of 'Toscana Friesia' primarily in flower color as plants of the new Zonal *Geranium* had more intense red-colored flowers than plants of 'Toscana Friesia'. In addition, plants of the new Zonal *Geranium* were more uniform and more rounded than plants of 'Toscana Friesia'.

BRIEF DESCRIPTION OF THE PHOTOGRAPH

The accompanying colored photograph illustrates the overall appearance of the new Zonal *Geranium* plant, showing the colors as true as it is reasonably possible to obtain in colored reproductions of this type. Colors in the photograph may differ slightly from the color values cited in the detailed botanical description which accurately describe the colors of the new Zonal *Geranium*.

The photograph comprises a side perspective view of a typical flowering plant of 'Fipelsumtrur' grown in a container.

DETAILED BOTANICAL DESCRIPTION

The aforementioned photograph and following observations, measurements and values describe plants grown in De Lier, The Netherlands in a glass-covered greenhouse during the summer and under conditions which closely approximate commercial production. During the production of the plants, day temperatures ranged from 17° C. to 18° C. and night temperatures ranged from 14° C. to 16° C. Plants were 13 weeks old when the photograph and the description were taken. In the detailed description, color references are made to The Royal Horticultural Society Colour Chart, 2001 Edition, except where general terms of ordinary dictionary significance are used.

Botanical classification: *Pelargonium×hortorum 'Fipelsumtrur'*.

Parentage:

*Female, or seed, parent.*—Unnamed proprietary selection of *Pelargonium×hortorum*, not patented.

*Male or pollen parent.*—Unnamed proprietary selection of *Pelargonium×hortorum*, not patented.

Propagation:

*Type.*—By vegetative terminal cuttings.

*Time to initiate roots, summer.*—About four days at temperatures of 22° C.

*Time to initiate roots, winter.*—About seven days at temperatures of 22° C.

*Time to produce a rooted young plant, summer.*—About 16 days at temperatures of 22° C. to 30° C.

*Time to produce a rooted young plant, winter.*—About 21 days at temperatures of 20° C. to 25° C.

*Root description.*—Medium in thickness, fibrous; whitish grey in color.

*Rooting habit.*—Moderately freely branching, moderately dense.

Plant description:

*General appearance.*—Upright and somewhat outwardly spreading growth habit; rounded and uniformly mounded plant habit; densely foliated.

*Growth and branching habit.*—Moderately vigorous to vigorous growth habit. Freely basal branching habit with about five to seven basal branches developing per plant.

*Plant height, to top of umbels.*—About 19 cm to 20 cm.

*Plant height, to top of foliar plane.*—About 10 cm.

*Plant width.*—About 22 cm to 26 cm.

*Lateral branches.*—Length: About 6 cm to 8 cm. Diameter: About 5 mm to 8 mm. Internode length: About 1 cm to 3 cm. Texture: Pubescent. Strength: Moderately strong. Color: Close to 144B.

Foliage description:

*Arrangement.*—Alternate; simple.

*Length (including petiole).*—About 5.5 cm.

*Width.*—About 8 cm.

*Shape.*—Orbicular.

*Apex.*—Acute.

*Base.*—Cordate.

*Margin.*—Slightly crenate.

*Venation pattern.*—Palmate.

*Texture, upper surface.*—Smooth, glabrous.

*Texture, lower surface.*—Pubescent.

*Color.*—Developing foliage, upper surface: Close to 137B. Developing foliage, lower surface: Close to 147B. Fully developed, upper surface: Close to N137A; venation, close to 137D. Fully developed, lower surface: Close to 147B; venation, close to 137C. Zonation pattern: Intensity: Distinct. Width: About 1 cm. Color: Close to 177A.

*Petiole.*—Length: About 4 cm to 5 cm. Diameter: About 2 mm to 3 mm. Texture, upper and lower surfaces: Pubescent. Color, upper and lower surfaces: Close to 146A.

Flower description:

*Flower arrangement.*—Semi-double rotate flowers arranged in rounded hemispherical umbels arising from apical leaf axils. Umbels displayed above the foliage on strong peduncles. Flowers face upright to outward. Flowers not fragrant.

*Quantity of flowers.*—Freely flowering habit; about nine to eleven umbels develop per plant, each umbel with about 60 to 65 flowers.

*Flowering season.*—Plants begin flowering about six to eight weeks after planting. In The Netherlands, flowering is continuous from late spring until frost in the autumn.

*Flower longevity.*—Individual flowers last about 2 to 14 days on the plant; flowers persistent.

*Umbel height.*—About 9 cm.

*Umbel diameter.*—About 11 cm to 12 cm.

*Flower diameter.*—About 5 cm.

*Flower depth (height).*—About 1.4 cm to 2 cm.

*Flower buds.*—Length: About 1.5 cm to 2 cm. Diameter: About 5 mm to 10 mm. Shape: Globular to elliptical. Color: Close to 146B.

*Petals.*—Quantity per flower: About eight to ten. Length: About 2.2 cm to 2.4 cm. Width: About 2 cm to 2.2 cm. Shape: Spatulate to obovate. Apex: Obtuse. Base: Attenuate. Margin: Entire. Texture, upper and lower surfaces: Smooth, glabrous; velvety. Color: When opening and fully opened, upper surface: Close to 46B; with development, color becoming closer to 53A. When opening and fully opened, lower surface: Close to 46C; with development, color becoming closer to 53C.

*Petaloids.*—Quantity per flower: If present, up to three. Length: About 1 cm to 1.5 cm. Width: About 1 mm to 3 mm. Shape: Irregularly shaped; obovate to irregularly oblanceolate. Apex: Obtuse. Base: Attenuate. Margin: Entire. Texture, upper and lower surfaces: Smooth, glabrous; velvety. Color: When opening, upper and lower surfaces: Close to 46B. Fully opened, upper and lower surfaces: Close to 46C.

*Sepals.*—Quantity per flower: Five, arranged in a single whorl. Length: About 1 cm. Width: About 3 mm. Shape: Oblong to ovate. Apex: Acute. Base: Lobate to truncate. Margin: Entire. Texture, upper and lower surfaces: Densely pubescent. Color, upper surface: Close to 143C. Color, lower surface: Close to N137A.

*Peduncle (umbel stem).*—Length: About 10 cm to 12 cm. Diameter: About 3 mm to 4 mm. Strength: Strong. Angle: Erect to about 30° C. from vertical. Texture: Pubescent. Color: Close to 146A.

*Pedicel (individual flower stem).*—Length: About 2.5 cm. Diameter: About 1 mm to 2 mm. Strength: Moderately strong. Angle: Erect to about 60° C. from vertical. Texture: Pubescent. Color: Close to 178A.

*Reproductive organs.*—Androecium: Stamen quantity per flower: About one to ten. Filament length: About 5 mm to 6 mm. Filament color: Close to 155A. Anther length: About 2 mm to 3 mm. Anther shape: Oblong. Anther color: Close to 70B. Pollen amount: Moderate. Pollen color: Close to 33B. Gynoecium: Pistil quantity per flower: One. Pistil length: About 9 mm to 12 mm. Stigma shape: Tapering; reflexed. Stigma color: Close to N79B. Style length: About 4 mm to 5 mm. Style color: Close to N79B. Ovary color: Close to N79B.

*Fruits/seeds.*—Fruit and seed development have not been observed.

Disease/pest resistance: Plants of the new Zonal *Geranium* have not been observed to be resistant to pathogens and pests common to Zonal *Geraniums*.

Garden performance: Plants of the new Zonal *Geranium* have been observed to tolerate rain, wind, and temperatures ranging from about 0° C. to about 40° C. and have demonstrated good garden performance.

It is claimed:

1. A new and distinct Zonal *Geranium* plant named 'Fipelsumtrur' as illustrated and described.

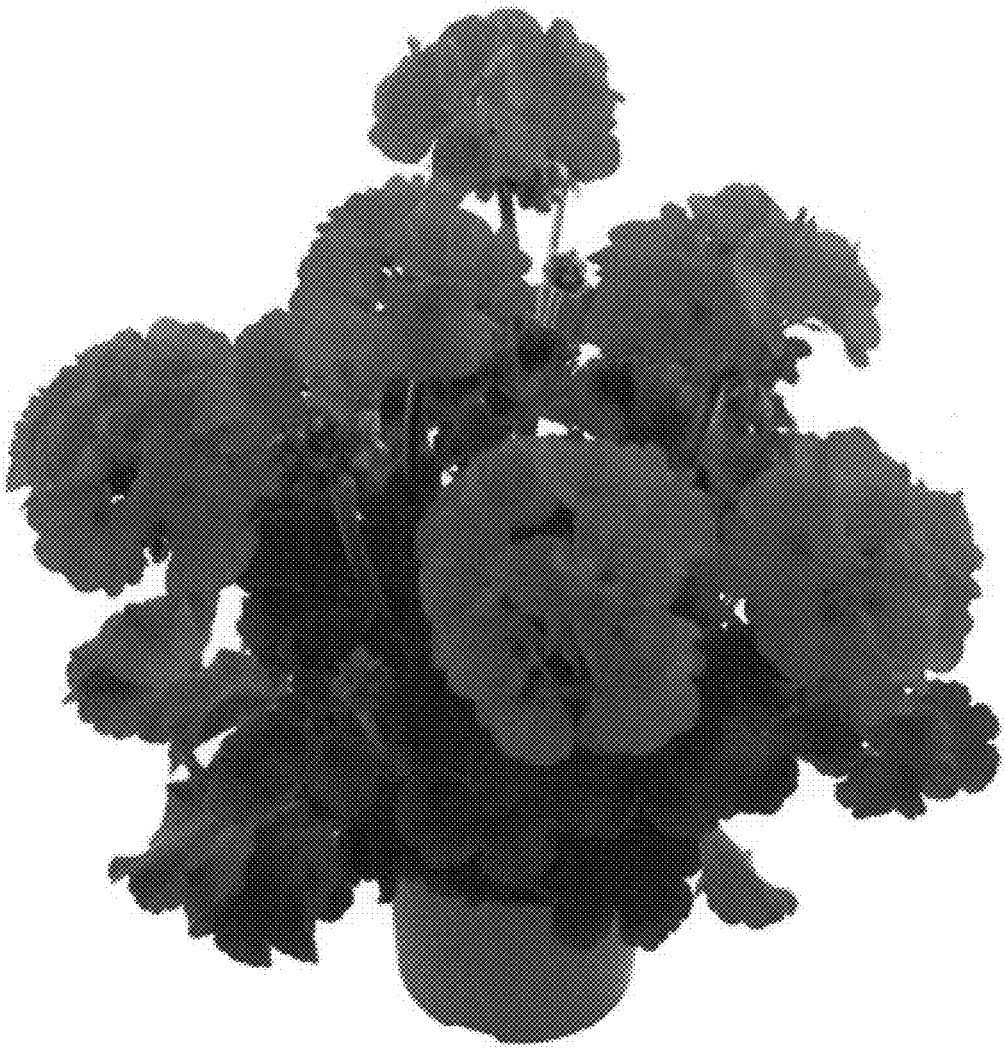

* * * * *